(12) United States Patent
   Dill

(10) Patent No.: US 11,439,804 B1
(45) Date of Patent: Sep. 13, 2022

(54) MEDICAL TUBING ORGANIZER

(71) Applicant: Tucky Dill, Ray, MN (US)

(72) Inventor: Tucky Dill, Ray, MN (US)

( * ) Notice: Subject to any disclaimer, the term of this patent is extended or adjusted under 35 U.S.C. 154(b) by 0 days.

(21) Appl. No.: 17/204,585

(22) Filed: Mar. 17, 2021

Related U.S. Application Data

(60) Provisional application No. 62/991,258, filed on Mar. 18, 2020.

(51) Int. Cl.
   *A61M 39/08* (2006.01)
   *F16C 11/06* (2006.01)

(52) U.S. Cl.
   CPC ............ *A61M 39/08* (2013.01); *F16C 11/06* (2013.01); *A61M 2209/082* (2013.01)

(58) Field of Classification Search
   CPC ... A61M 39/08; A61M 2209/082; F16C 11/06
   USPC .................... 248/225.11, 230.5, 231.61, 68.1
   See application file for complete search history.

(56) References Cited

U.S. PATENT DOCUMENTS

| | | | |
|---|---|---|---|
| 4,025,015 A * | 5/1977 | Kolic ........................ | F16L 3/08 248/229.11 |
| D263,624 S * | 3/1982 | Stenzler ........................ | D24/128 |
| 4,971,271 A | 11/1990 | Sularz | |
| 6,375,017 B1 * | 4/2002 | Schattner ............ | A61M 5/1418 604/80 |
| 6,458,104 B2 | 10/2002 | Gautsche | |
| 6,752,360 B2 * | 6/2004 | Bennett .................. | F16L 3/2235 248/89 |
| 7,918,828 B2 | 4/2011 | Lundgaard et al. | |
| D683,849 S * | 6/2013 | Breckon ...................... | D24/128 |
| 9,920,858 B2 * | 3/2018 | Harnetiaux ............. | F16L 3/223 |
| 2003/0132352 A1 | 7/2003 | Weaver | |
| 2004/0118982 A1 * | 6/2004 | Shillings .................. | F16L 3/223 248/68.1 |
| 2005/0077436 A1 * | 4/2005 | Nelson ..................... | F16L 3/223 248/68.1 |
| 2006/0113432 A1 | 6/2006 | Driskell | |
| 2008/0097333 A1 | 4/2008 | Henning | |
| 2011/0248125 A1 | 10/2011 | D'Andria | |
| 2014/0306070 A1 | 10/2014 | Hartsock et al. | |
| 2015/0358044 A1 * | 12/2015 | Barstead .............. | H04B 1/3888 455/575.1 |
| 2020/0306117 A1 * | 10/2020 | Moudy ................ | A61G 13/107 |

* cited by examiner

*Primary Examiner* — Muhammad Ijaz
(74) *Attorney, Agent, or Firm* — Hamre, Schumann, Mueller & Larson, P.C.

(57) ABSTRACT

A medical tubing organizer that includes a tube holding portion configured to hold a plurality of medical tubes, and a mounting portion that is configured to mount to a support structure. The tube holding portion and the mounting portion are connected to one another by a connection mechanism, for example a ball and socket, that permits pivoting of the tube holding portion and the mounting portion relative to one another. The tube holding portion can include a plurality of tines, and a gap between adjacent pairs of the tines with each adjacent pair of tines having facing surfaces that are scalloped and defining tube holders having different sizes.

12 Claims, 4 Drawing Sheets

MEDICAL TUBING ORGANIZER

FIELD

This technical disclosure relates to an organizer for organizing medical tubes and medical cables connected to a patient.

BACKGROUND

A patient receiving medical treatment at a hospital, nursing home, in their home or at any other place of treatment may be simultaneously connected to numerous tubes and cables associated with their treatment, such as IV lines and monitoring devices. Examples of efforts at organizing the tubes and cables include the devices described in US 2003/0132352, US 2004/0118982, US 2005/0077436, US 2006/0113432, US 2008/0097333, US 2011/0248125, US 2014/0306070, U.S. Pat. Nos. 4,971,271, 6,458,104, and 7,918,828.

SUMMARY

An organizer for medical tubes and medical cables connected or connectable to a patient is described. The organizer is configured to hold and organize the various medical tubes and medical cables that may be connected to a patient receiving treatment, for example in a hospital, a nursing home, the patient's home, or other facility where the patient may be receiving treatment. In one embodiment, the organizer described herein is configured to be removably mounted to a rail of a bed that the patient is occupying. However, in other embodiments, the organizer or parts of the organizer can be mounted at other locations, for example to other medical equipment such as an IV stand, and even mounted to bedding, the patient gown, or to the patient.

The organizer described herein has two primary parts, namely a tube holding portion that is configured to hold the medical tubes and/or the medical cables, and a mounting portion for mounting the organizer to a suitable mounting location. In one embodiment, the organizer is formed entirely of non-metallic material, for example formed entirely of plastic material, allowing the organizer to be used in any area of a medical facility. However, in some embodiments, portions or all of the organizer may be made of metal material. In one embodiment, the organizer may be made of a material so that it is disposable after a single use and/or recyclable. In other embodiments, the organizer may be made of a material allowing the organizer to be sterilized so that the organizer can be used multiple times and intending to be sterilized after each use.

In one embodiment, a medical tubing organizer described herein can include a tube holding portion that is configured to hold a plurality of medical tubes, and a mounting portion that is configured to mount to a structure. The tube holding portion and the mounting portion are connected to one another by a connection mechanism that permits pivoting of the tube holding portion and the mounting portion relative to one another. For example, the connection mechanism can be a ball and socket joint that permits pivoting including, but not limited to, universal movement. However, other types of connection mechanisms can be used.

In still another embodiment, a medical tubing organizer described herein can include a tube holding portion that is configured to hold a plurality of medical tubes and a mounting portion that is configured to mount to a structure. The tube holding portion can include a plurality of tines that extend in a first direction parallel to one another from a first, fixed end to a second, distal end. There is a gap between adjacent pairs of the tines with each adjacent pair of tines having facing surfaces that are scalloped. The facing surfaces of each adjacent pair of tines define a plurality of tube holders having different sizes.

The tube holding portion and the mounting portion may be provided as separate or replacement parts. Therefore, in one embodiment, a tube holding portion of a medical tubing organizer can include a plurality of tines that extend in a first direction parallel to one another from a first, fixed end to a second, distal end. There is a gap between adjacent pairs of the tines with each adjacent pair of tines having facing surfaces that are scalloped. The facing surfaces of each adjacent pair of tines define a plurality of tube holders having different sizes.

DRAWINGS

DETAILED DESCRIPTION

Figure 1:
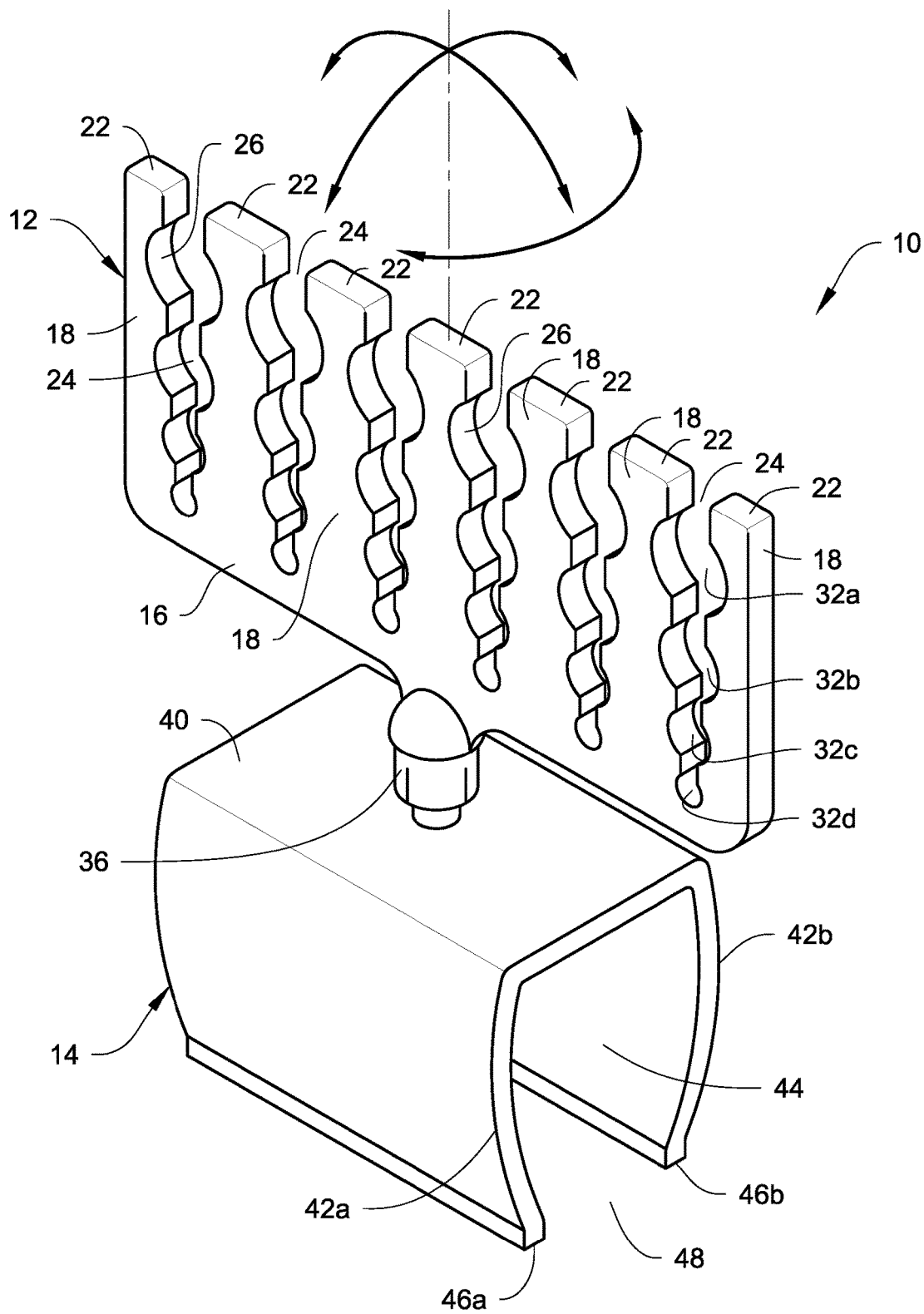
FIG. 1 is a perspective view of an example of a medical tubing organizer described herein.
Figure 2:
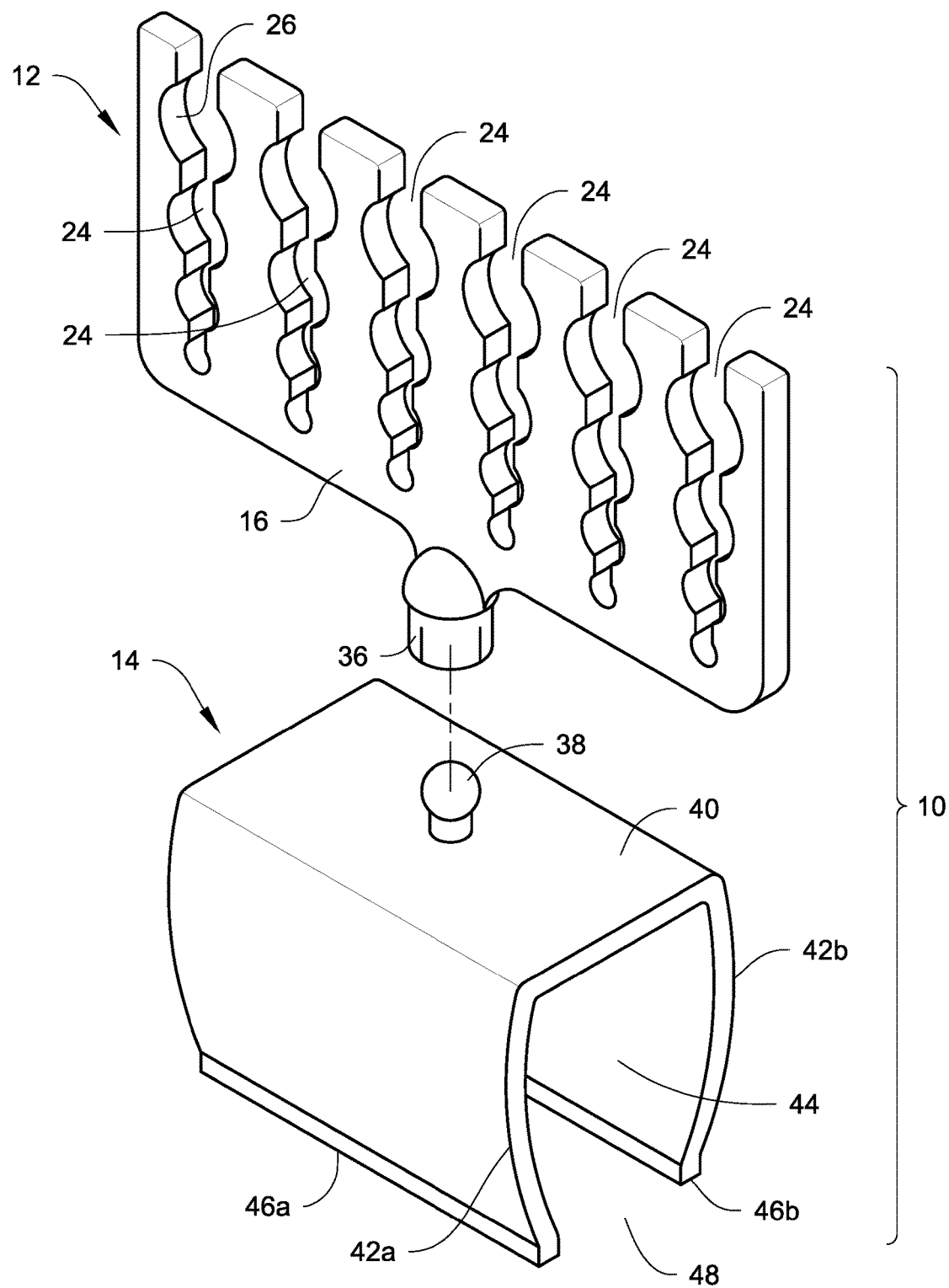
FIG. 2 is an exploded view of the tube holding portion and the mounting portion of the medical tubing organizer of FIG. 1.
Figure 3:
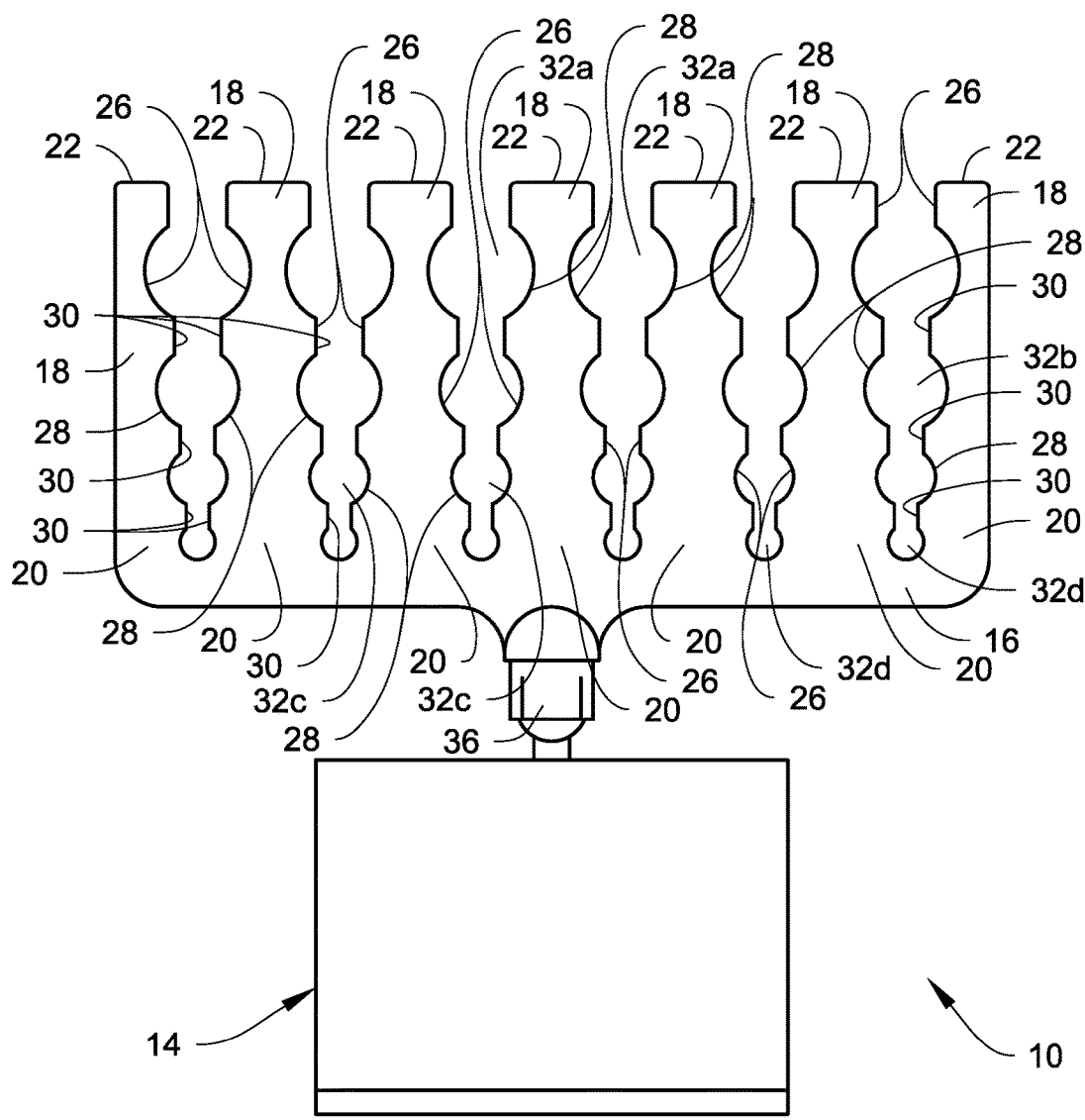
FIG. 3 is a side view of the tube holding portion and the mounting portion of the medical tubing organizer.

Referring to FIGS. 1-3, a medical tubing organizer 10 described herein is illustrated. The medical tubing organizer 10 is configured to hold and organize medical tubes and medical cables connected or connectable to a patient receiving treatment. The medical tubes may be delivering fluids to or leading fluids from the patient. Examples of medical tubes include, but are not limited to, IV tubes and catheters. The medical cables electrically connect various sensors on the patient to monitoring equipment. Examples of medical cables include, but are not limited to, EKG leads. So the language "medical tubing organizer" as used herein and in the claims is intended to encompass organizing not only medical tubes but also medical cables.

The organizer 10 includes a tube holding portion 12 and a mounting portion 14. The tube holding portion 12 is configured in such a manner to simultaneously hold and organize a plurality of medical tubes and/or medical cables. The mounting portion 14 is configured in such a manner to mount the organizer 10 to a suitable mounting location.

As best seen in FIGS. 1-3, the tube holding portion 12 incudes a base 16 and a plurality of tines 18 that extend upwardly from the base 16 in a first direction parallel to one another from a first end 20 fixed to the base 16 to a second, distal or tip end 22. There is a gap 24 between each adjacent pair of the tines 18 with the gaps 24 extending from the ends 20 to the ends 22, and each adjacent pair of tines 18 has facing surfaces 26 that define the gap 24. Each one of the surfaces 26 is scalloped including a plurality of concave portions 28 (or valleys) and peaks 30, which are illustrated as being flat, between the concave portions 28. The gaps 24 between the tines 18 increase in size from the base 16 toward the ends 22. In addition, the radius of the concave portions 28 varies; in the illustrated example, within each one of the gaps 24, the radius of the concave portions 28 increases from the base 16 toward the ends 22. Further, the concave portions 28 and the peaks 30 on the facing surface 26 defining each gap 24 are aligned. The result is that the facing surfaces 26 of each adjacent pair of tines 18 define a plurality of tube holders 32a, 32b, 32c, 32d that have different sizes (i.e. diameters). In the illustrated example, the tube holders 32a, 32b, 32c, 32d increase in size from the base 16 toward the ends 22, with a largest size tube holder 32d near the ends 22 and a smallest size tube holder 32a near the ends 20. The tube holders 32a, 32b, 32c, 32d permit the organizer 10 to simultaneously accommodate and hold different diameter medical tubes, possibly without pinching the tubes or restricting flow through the tubes. Although FIG. 1-4 illustrate the organizer 10 as including six of the gaps 24 and four of the tube holders 32a, 32b, 32c, 32d in each gap 24, the organizer 10 can include a larger or smaller number of gaps 24 and tines 18, as well as include a larger or smaller number of tube holders in each gap.

The tube holding portion 12 further includes part of a connection mechanism that engages with a connection mechanism part on the mounting portion 14 to connect the tube holding portion 12 and the mounting portion 14. In one embodiment, the connection mechanism can permit relative movements between the tube holding portion 12 and the mounting portion 14 so that the orientation of the tube holding portion 12 relative to the mounting portion 14 can be changed. In one embodiment, the connection mechanism can have a configuration that permits pivoting movement of the tube holding portion 12 and the mounting portion 14 relative to one another. The connection mechanism can have any configuration that permits such pivoting movement. For example, the connection mechanism can be a ball and socket joint that permits universal movement. The illustrated example shows the tube holding portion 12 as including a cup-shaped socket 36 that extends downwardly from the base 16 in a direction opposite the tines 18 or parallel to the axes of the tines 18. The socket 36 receives a ball 38 (best seen in FIG. 2) that is fixed to the mounting portion 14 and extends upwardly therefrom.

In one embodiment, the socket 36 and the ball 38 can be configured to permit the tube holding portion 12 and the mounting portion 14 to be detached from one another (see FIG. 2) in which case the ball 38 is releasably disposed in the socket 36. It is preferred that the tube holding portion 12 and the mounting portion 14 be manually detachable from one another without the use of mechanical tools such as screwdrivers or wrenches. In addition, the ball 38 can be part of the tube holding portion 12 and the socket 36 can be part of the mounting portion 14.

Referring to FIGS. 1 and 2, the mounting portion 14 can have any configuration that is suitable for releasably mounting the organizer 10 on a support structure. In the illustrated example, the mounting portion 14 is configured as a generally C-shaped clamp that includes a top plate 40 on which the ball 38 is secured, and opposing arms 42a, 42b that extend downwardly from opposite sides of the plate 40. The arms 42a, 42b are illustrated as being slightly curved toward one another and the arms 42a, 42b are resiliently biased toward one another. The top plate 40 and the arms 42a, 42b define a channel 44 that is open at both ends, and free ends 46a, 46b of the arms 42a, 42b define a gap 48 therebetween leading to/from the channel 44. The gap 48 permits the mounting portion 14, and thus the organizer 10, to be removably installed onto a suitable support structure, such as a rail of a bed that the patient is occupying or other support structure that the mounting portion 14 can mount to, with the support structure received in the channel 44. In one embodiment, the gap 48 is sized to be smaller than the size of the support structure so that the free ends 46a, 46b of the arms 42a, 42b must be deflected away from one another in order to fit onto the support structure and so that the resilient bias of the arms 42a, 42b clamps the mounting portion 14 onto the support structure. In addition, once mounted, the channel 44 permits the mounting portion 14 to be slid along a length of the support structure to adjust the position of the mounting portion 14, and thus the organizer 10, relative to the support structure.

In operation of the organizer, the tube holding portion 12 and the mounting portion 14 are connected to one another by the cup-shaped socket 36 and the ball 38. The relative positions of the tube holding portion 12 and the mounting portion 14 can be adjusted as permitted by the socket 36 and ball 38. The friction between the socket 36 and the ball 38 is sufficient to prevent free or casual movement between the tube holding portion 12 and the mounting portion 14, but permit manual adjustment of the relative positions of the tube holding portion 12 and the mounting portion 14 using ones hands. The mounting portion 14 can be mounted to a support structure, which can occur with or without the tube holding portion 12 secured to the mounting portion 14.

The components of the organizer 10 can be made of any material that is suitable for a medical environment. For example, in one embodiment, the tube holding portion 12 and the mounting portion 14, including the socket 36 and the ball 38, can be formed entirely of non-metallic material, for example plastic. The components of the organizer 10 can be formed by any suitable fabrication technique including, but not limited to, molding or 3D printing. In one embodiment, the organizer 10 may be disposed after a single use. In another embodiment, the organizer 10 may be recycled after use. In still another embodiment, the organizer 10 may be sterilized after use so that the organizer 10 can be used multiple times.

Figure 4:
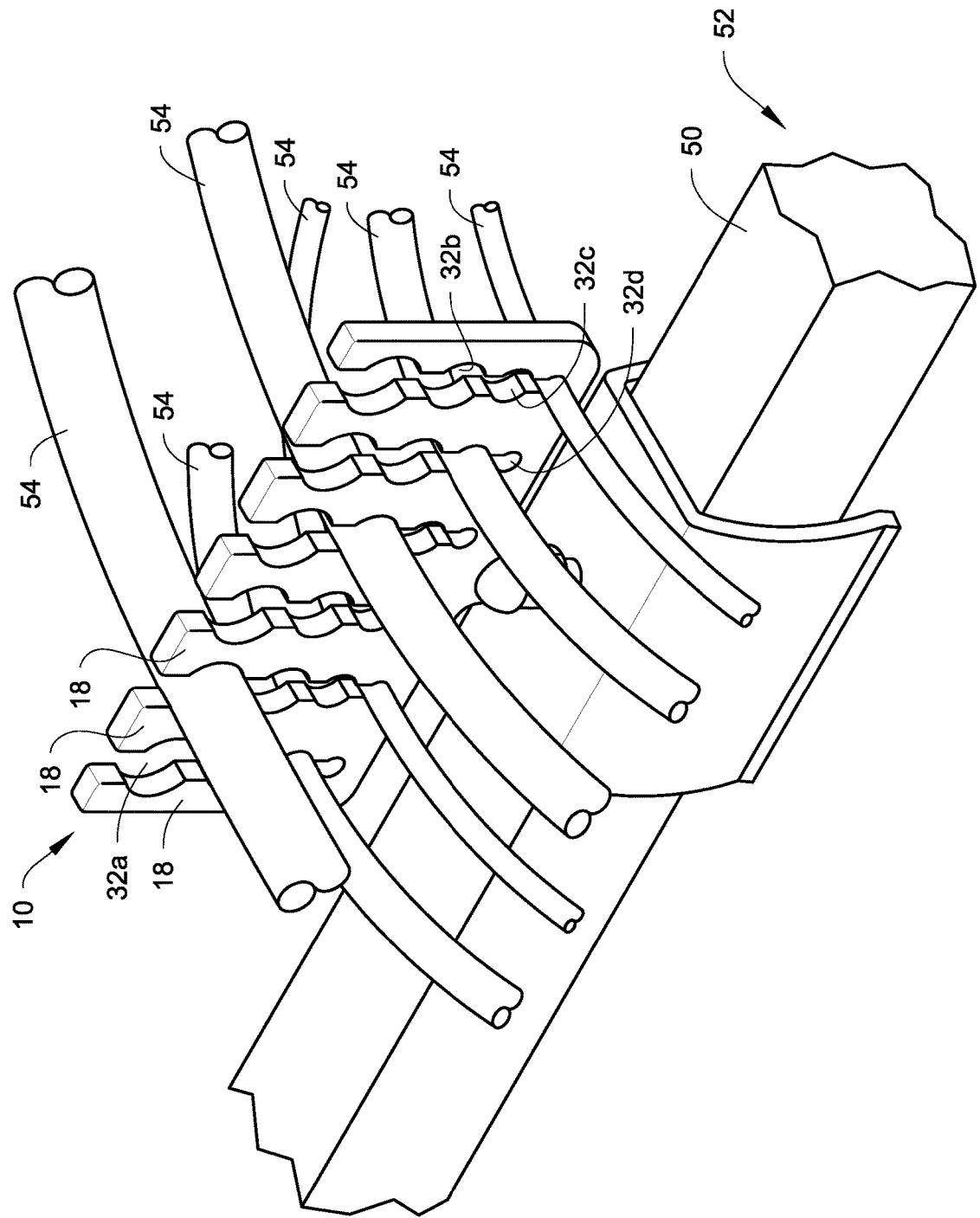
FIG. 4 illustrates an example use of the medical tubing organizer mounted on a rail of a bed.

Referring now to FIG. 4, an example operation of the organizer 10 is depicted. The organizer 10 is depicted as being mounted on a rail 50 of a bed 52. A plurality of medical tubes and/or cables 54 of different sizes (i.e. diameters) leading to/from a patient are depicted as being held in the tube holders 32a, 32b, 32c, 32d of the tube holding portion 12. In some embodiments, due to the varying size of the tube holders 32a, 32b, 32c, 32d, more than one tube and/or cable 54 can be held in the gap between two adjacent tines 18. The tube/cable 54 will not come out of the tube holder 32a, 32b, 32c, 32d unless it is manually pulled out. In addition, the organizer can be used on the bed 52 with the rail 50 either in an up position or a down position.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:
1. A medical tubing organizer, comprising:
a tube holding portion that is configured to hold a plurality of medical tubes, the tube holding portion comprises a plurality of tines that extend in a first direction parallel to one another from a first, fixed end to a second, distal end; a gap between adjacent pairs of the tines with each said adjacent pair of tines having facing surfaces that are scalloped to include a plurality of concave portions and peaks; and the facing surfaces of each adjacent pair of tines define a plurality of tube holders having different sizes;

a mounting portion that is configured to mount to a structure, the mounting portion comprises a clamp that includes a top plate with opposite sides and opposing arms that extend downwardly from the opposite sides of the top plate in a direction opposite the first direction;

wherein the tube holding portion and the mounting portion are connected to one another by a ball and socket joint so that the tube holding portion and the mounting portion can move relative to one another, the ball and socket joint includes a ball and a socket, and the ball or the socket are attached directly to the top plate.

2. The medical tubing organizer of claim 1, wherein the socket is attached directly to the tube holding portion, and the ball is attached directly to the top plate of the mounting portion.

3. The medical tubing organizer of claim 2, wherein the socket extends downwardly from the tube holding portion in the direction opposite the first direction.

4. The medical tubing organizer of claim 1, wherein the opposing arms are resiliently biased toward one another.

5. The medical tubing organizer of claim 1, wherein the tube holding portion, the mounting portion and the ball and socket joint are formed entirely of non-metallic material.

6. The medical tubing organizer of claim 5, wherein the tube holding portion, the mounting portion and the ball and socket joint are formed entirely of plastic.

7. The medical tubing organizer of claim 1, wherein the different sizes of the tube holders are arranged so that a largest size tube holder is near the second, distal end and a smallest size tube holder is near the first, fixed end.

8. A medical tubing organizer, comprising:
a tube holding portion that is configured to hold a plurality of medical tubes;
a mounting portion that is configured to mount to a structure;
wherein the tube holding portion comprises a plurality of tines that extend in a first direction parallel to one another from a first, fixed end to a second, distal end;
a gap between adjacent pairs of the tines with each said adjacent pair of tines having facing surfaces that are scalloped to include a plurality of concave portions and peaks; and the facing surfaces of each adjacent pair of tines define a plurality of tube holders having different sizes;
the mounting portion comprises a clamp that includes a top plate with opposite sides and opposing arms that extend downwardly from the opposite sides of the top plate in a second direction opposite the first direction;
a universal connection mechanism that connects the tube holding portion to the mounting portion, the universal connection mechanism is configured to permit universal movement between the tube holding portion and the mounting portion.

9. The medical tubing organizer of claim 8, wherein the different sizes of the tube holders are arranged so that a largest size tube holder is near the second, distal ends and a smallest size tube holder is near the first, fixed end.

10. The medical tubing organizer of claim 8, wherein the opposing arms are resiliently biased toward one another.

11. The medical tubing organizer of claim 8, wherein the tube holding portion and the mounting portion are formed entirely of non-metallic material.

12. The medical tubing organizer of claim 11, wherein the tube holding portion and the mounting portion are formed entirely of plastic.

* * * * *